US008010202B2

(12) United States Patent
Shah et al.

(10) Patent No.: US 8,010,202 B2
(45) Date of Patent: *Aug. 30, 2011

(54) METHOD OF IMPROVING ELECTRODE TISSUE INTERFACE

(75) Inventors: Samip Shah, Lake Forest, CA (US); Amy Chu Peishuan Hines, Monterey Park, CA (US); Dao Min Zhou, Saugus, CA (US); Robert J. Greenberg, Los Angeles, CA (US); Mark S. Humayun, Glendale, CA (US); James D. Weiland, Valencia, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 404 days.

This patent is subject to a terminal disclaimer.

(21) Appl. No.: 11/943,487

(22) Filed: Nov. 20, 2007

(65) Prior Publication Data
US 2008/0119908 A1 May 22, 2008

Related U.S. Application Data

(60) Provisional application No. 60/860,388, filed on Nov. 20, 2006.

(51) Int. Cl.
*A61N 1/00* (2006.01)
(52) U.S. Cl. ........................................ 607/54
(58) Field of Classification Search .............. 607/54
See application file for complete search history.

(56) References Cited

U.S. PATENT DOCUMENTS

| 4,573,481 | A | 3/1986 | Bullara |
| 4,628,933 | A | 12/1986 | Michelson |
| 4,837,049 | A | 6/1989 | Byers et al. |
| 5,109,844 | A | 5/1992 | de Juan, Jr. et al. |
| 5,215,088 | A | 6/1993 | Normann et al. |
| 5,341,807 | A | * 8/1994 | Nardella ............... 600/381 |
| 5,935,155 | A | 8/1999 | Humayun et al. |
| 6,400,989 | B1 | 6/2002 | Eckmiller |
| 6,458,157 | B1 | 10/2002 | Suaning |
| 6,974,533 | B2 | 12/2005 | Zhou |
| 7,181,287 | B2 | 2/2007 | Greenberg |
| 2002/0111658 | A1 | 8/2002 | Greenberg et al. |
| 2003/0195601 | A1 | 10/2003 | Hung et al. |
| 2004/0220652 | A1 | 11/2004 | Zhou et al. |

(Continued)

OTHER PUBLICATIONS

Mahadevappa et al. Perceptual Thresholds and Electrode Impedance in Three Retinal Prosthesis Subjects. IEEE Transactions on Neural Systems and Rehabilitation Engineering. Jun. 2005; 13,2: 201-206.*

(Continued)

*Primary Examiner* — Carl H Layno
*Assistant Examiner* — Jeremiah T Kimball
(74) *Attorney, Agent, or Firm* — Scott B. Dunbar; Alessandro Steinfl

(57) ABSTRACT

A critical element of a retinal prosthesis is the stimulating electrode array, which is placed in close proximity to the retina. It is via this interface that a retinal prosthesis electrically stimulates nerve cells to produce the perception of light. The impedance load seen by the current driver consists of the tissue resistance and the complex electrode impedance. The results show that the tissue resistance of the retina is significantly greater than that of the vitreous humor in the eye. Circuit models of the electrode-retina interface are used to parameterize the different contributors to the overall impedance.

17 Claims, 6 Drawing Sheets

U.S. PATENT DOCUMENTS

| | | |
|---|---|---|
| 2005/0271895 A1 | 12/2005 | Zhou |
| 2006/0063062 A1 | 3/2006 | Zhou et al. |
| 2006/0247754 A1 | 11/2006 | Greenberg et al. |
| 2006/0259108 A1 | 11/2006 | Hung et al. |
| 2006/0259109 A1 | 11/2006 | Zhou et al. |
| 2006/0259112 A1 | 11/2006 | Greenberg et al. |
| 2007/0026048 A1 | 2/2007 | Greenberg |
| 2007/0089992 A1 | 4/2007 | Zhou |
| 2007/0089994 A1 | 4/2007 | Zhou |
| 2007/0092750 A1 | 4/2007 | Zhou |
| 2007/0092786 A1 | 4/2007 | Zhou |
| 2007/0173905 A1 | 7/2007 | Greenberg et al. |
| 2007/0191911 A1 | 8/2007 | Greenberg et al. |
| 2007/0265665 A1 | 11/2007 | Greenberg et al. |

OTHER PUBLICATIONS

Humayun et al. Visual Perception in a Blind Subject with a Chronic Microelectronic Retinal Prosthesis. Vision Research. 2003; 43:24:2573-2581.*

Ratanapakorn et al. Enucleated Eye Model for Intraocular Retinal Prosthesis Implantation. Ophthalmic Surgery, Lasers and Imaging. vol. 37, No. 4 (Jul./Aug. 2006).*

Shah et al. Intraocular impedance as a function of the position in the eye, electrode material and electrode size. Conf Proc IEEE Eng Med Biol Soc. 2004;6:4169-71.*

Eugene De Juan, Retinal Tacks, American Journal of Ophthalmology 99: pp. 272-274, Mar. 1985.

* cited by examiner

METHOD OF IMPROVING ELECTRODE TISSUE INTERFACE

CROSS-REFERENCE TO RELATED APPLICATIONS

This application claims benefit of U.S. Provisional Patent application Ser. No. 60/860,388, filed on Nov. 20, 2006 now abandoned, entitled "Electrical Properties of Retinal-Electrode Interface," the disclosure of which is incorporated herein by reference.

GOVERNMENT RIGHTS NOTICE

This invention was made with government support under grant No. R24EY12893-01. The government has certain rights in the invention.

FIELD OF THE INVENTION

The present invention relates to a method of improving the electrode tissue interface in a visual prosthesis.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 1 mm-5 mm, preferably 2 mm-3 mm, more preferably about 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular visual prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretial). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Opthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a visual prosthesis for use with the flat retinal array described in de Juan.

SUMMARY OF THE INVENTION

A critical element of a retinal prosthesis is the stimulating electrode array, which is placed in close proximity to the retina. It is via this interface that a retinal prosthesis electrically stimulates nerve cells to produce the perception of light. The impedance load seen by the current driver consists of the tissue resistance and the complex electrode impedance. The results show that the tissue resistance of the retina is significantly greater than that of the vitreous humor in the eye. Circuit models of the electrode-retina interface are used to parameterize the different contributors to the overall impedance. The invention involves a method of optimizing an electrode tissue interface which comprises placing an electrode in the vicinity of neural tissue; stimulating the neural tissue through said electrode; measuring the impedance of the electrode tissue interface; and altering the location of said electrode based on said impedance measurement.

BRIEF DESCRIPTION OF THE DRAWINGS

FIG. 3-1 is a set of graphs showing the relationship of impedance modulus, phase and electrode diameter.
FIG. 3-2 is a set of graphs showing the relationship of impedance modulus, phase and electrode diameter.

DETAILED DESCRIPTION OF THE PREFERRED EMBODIMENTS

Figure 1:
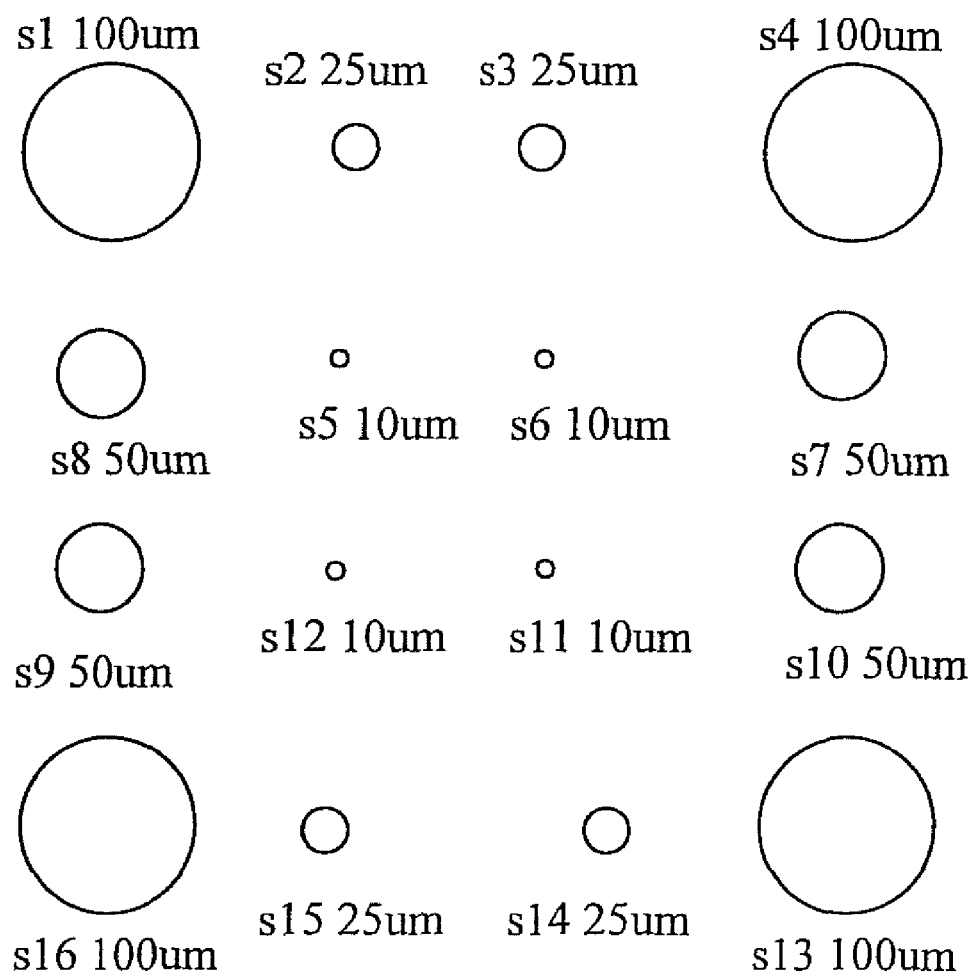
FIG. 1 is a diagram of the preferred electrode array layout.

Retinal prostheses are implantable electronic devices designed to electrically stimulate retinal neurons when the photoreceptors of the retina are absent, due to photoreceptor degenerative disease. Age-related macular degeneration and retinitis pigmentosa are two such diseases that blind millions worldwide. Several clinical trials of prototype retinal prostheses are currently on-going. All have shown the ability to evoke phosphenes (spots of light) in subjects otherwise blind. The systems are similar in their implementation. They use an external camera to capture light information, an external processor to code the image information and then wirelessly transmit stimulus commands to implants. The implants have custom circuits which decode the stimulus command signal and output electrical charge via a controlled current or voltage signal. The prototype devices all use electrical stimulation of retinal cells with extracellular electrodes as the means of creating a sensation of light in blind individuals.

The stimulating electrode is an important consideration when designing a retinal prosthesis. The impedance of the electrode and retina largely define the output load for the stimulator circuit, and thus the power consumption of the implanted system. It is desirable to have a dense interface, i.e. to put as many electrodes as possible in a small area of the retina, to achieve maximum visual acuity. This suggests that small diameter electrodes are preferable, but smaller electrodes have a number of negative consequences. These include higher impedance, which, for a given amount of stimulating current, requires a larger power supply for the stimulator chip and high charge density. Even if a charge balanced stimulus is used to make ensure no DC current, it is still possible to damage tissue if excessive charge density is used to stimulate. To guide the design of a retinal prosthesis, it is important to know the electrical interface properties. In this disclosure, the intraocular impedance is studied as a function of electrode location in the eye and electrode diameter.

The eye model used for these experiments was a cadaveric porcine eye, with an artificial cornea attached to allow viewing for retinal surgery. A smaller data set with in situ canine eye has been known, however it has been switched to cadaveric porcine eye for several reasons, including: 1) comparable results to the live canine eye 2) ease of use during implantation and surgery 3) increased availability, since the opportunity to perform canine experiments came only during terminal surgeries that involved other experiments. Several electrode array designs were tested. Features common to all designs include polyimide insulating layers as disclosed in U.S. patent applications Nos. 20060247754, 20060259112, and 20070265665, and circular, platinum electrodes as disclosed in U.S. Pat. Nos. 6,974,533 and 7,181,287 and U.S. patent applications Nos. 20020111658, 20070173905, 20070026048, 20030195601, 20060259108, 20050271895, 20060063062, 20040220652, 20060259109, 20070092786, 20070089994, 20070089992, 20070092750, and 20070191911, the disclosure of which are incorporated herein by reference.

The electrodes and insulating layers were coplanar. The electrode diameters tested include 50, 100, and 200 µm. Two array designs were used. Both arrays had a 4×4 arrangement of electrodes. One array had only 200 µm electrodes. The other array had 10, 25, 50, and 100 µm electrodes. The 10 and 25 µm diameter electrodes did not yield consistent results so these sizes were not included in further testing. The layout of the multi-size electrode is shown in FIG. 1. FIG. 1 shows electrode array layout used for testing. The electrode spacing was 800 µm center to center in the horizontal and vertical direction. An electrode with a similar layout, but with 200 µm diameter electrodes was also used.

For the cadaveric porcine eye (eye) surgery the eye was fixed in a Styrofoam holder. An infusion line was placed to maintain the pressure of the eye. Since the cornea and lens opacify shortly after enucleation, a false cornea (keratoprosthesis) was used to enable clear viewing of the vitreous cavity. A trephine was used to open a circular window in the cornea and the crystalline lens was removed through this opening. The keratoprosthesis was sutured into place in the window in the cornea. A standard three-port vitrectomy was performed to replace the vitreous gel with balanced salt solution (BSS), which is a standard vitreous replacement solution. To ensure that the electrode was in close contact with the retina, care was taken to remove as much vitreous as possible from the retinal surface. One sclerotomy wound was increased to 5 mm to accommodate insertion of the electrode array. After array insertion, the sclerotomies were closed so that minimal fluid was leaking from the eye, as determined by the drip rate of the infusion line. The electrode array was placed in the middle of the vitreous cavity for the first set of measurements. Then the electrode was placed on the retina for the second set of measurements. When placing the array on the retina, a retinal tack was used to ensure close placement.

AC impedance was measured using a commercial potentiostat (FAS1, Gamry Instruments, Inc.). The platinum test electrode was connected to the working electrode input and a large gold disc electrode (1 cm diameter, two sided) served as the counter and return electrode. The counter electrode was placed in contact with outside of the eye, on the opposite side of the eye from the large sclerotomy. Impedance was measured at 5 points/decade from 10 Hz to 100 kHz. The excitation signal was a 10 mV sine wave. No DC bias potential was applied so the electrode was at open circuit potential.

Figure 2:
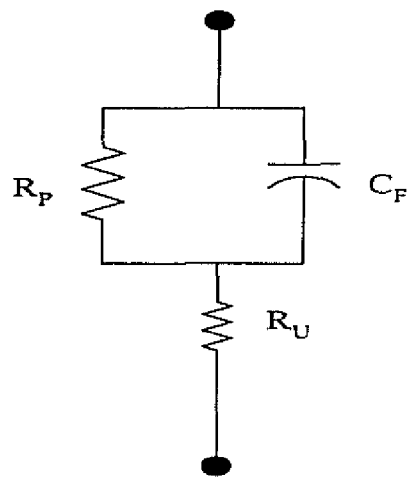
FIG. 2 is a schematic representation of the tissue electrode interface.

Circuit models were used to parameterize the different parts of the electrode-tissue impedance. A common model used to describe the electrode-electrolyte impedance spectrum is the three element model shown in FIG. 2. FIG. 2 shows a three element circuit model. $R_u$ represents tissue resistance, $C_F$ represents double layer capacitance, and $R_p$ represents Faradaic charge transfer. For this modeling, a CPE was substitute for $C_F$ and a parallel capacitance was added to account for parasitic system capacitance. Charge injection via the electrode can take place either via charging and discharging across the double layer capacitive layer represented by capacitance C of the model or through electrochemical reactions across the interface modeled by a parallel resistor. The electrolyte is modeled by a series resistance. Variations on this include use of a constant phase element (CPE) in place of the parallel capacitor when the electrode is roughened, as was the case in these studies. The CPE represents a network of resistors and capacitors, similar to a transmission line, and its impedance is expressed as $Z_{CPE}=Y_o(j\omega)^{-n}$. If n is close to 1, then the CPE is primarily capacitive, if n is close to 0 then the CPE is primarily resistive. Another element was included in the model to account for experimental conditions. A parasitic capacitance, due to long lead wires, was included in parallel with the entire model. This was evident as capacitive impedance at high frequency. Models were constructed and fit using software from Gamry, Inc.

Figures 1, 3:
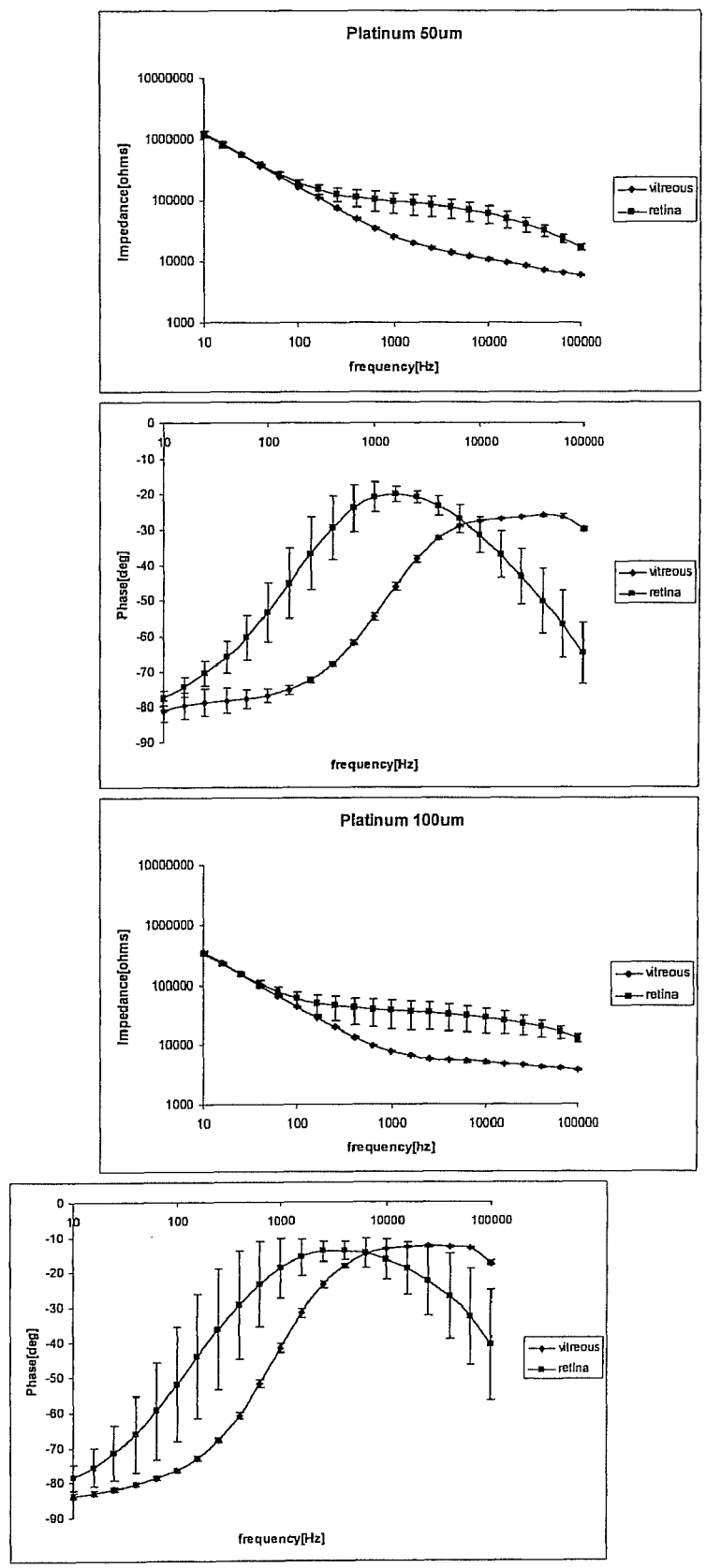
Figures 2, 3:
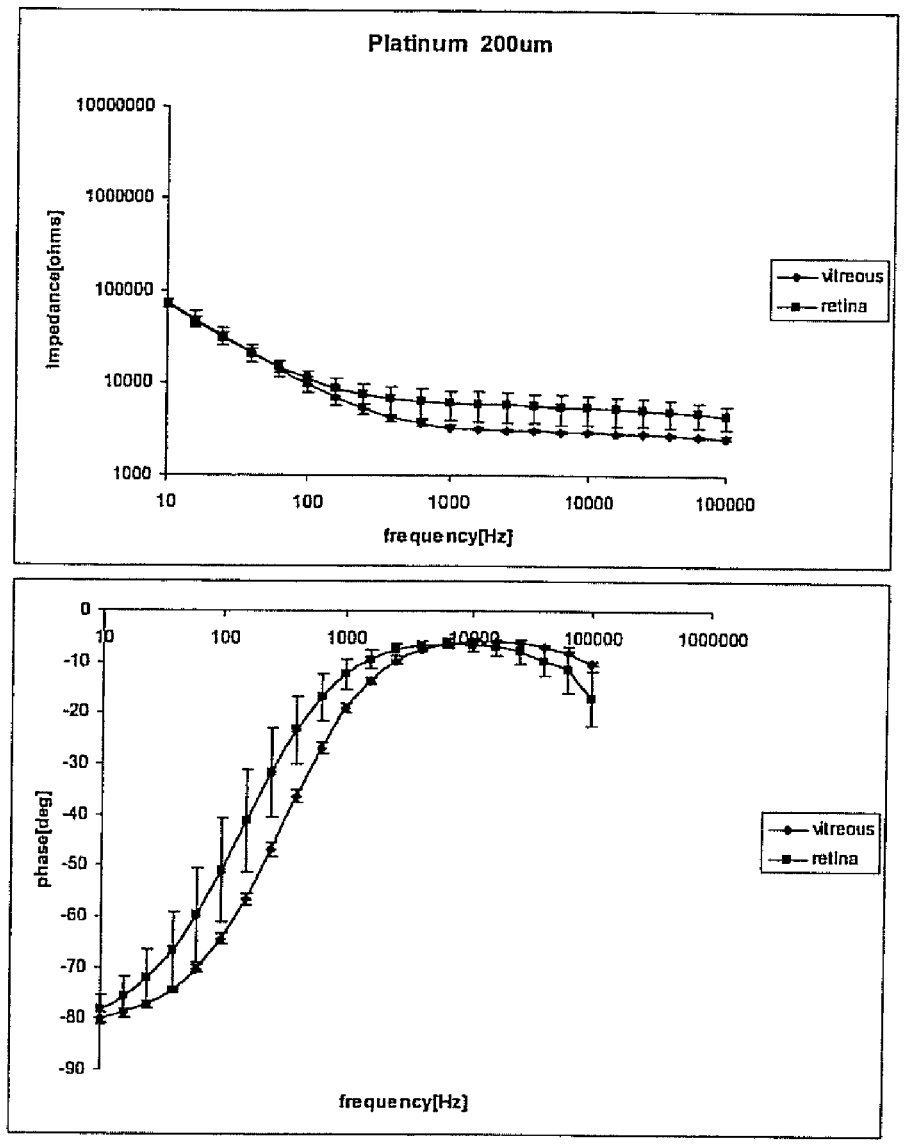
Figure 4:
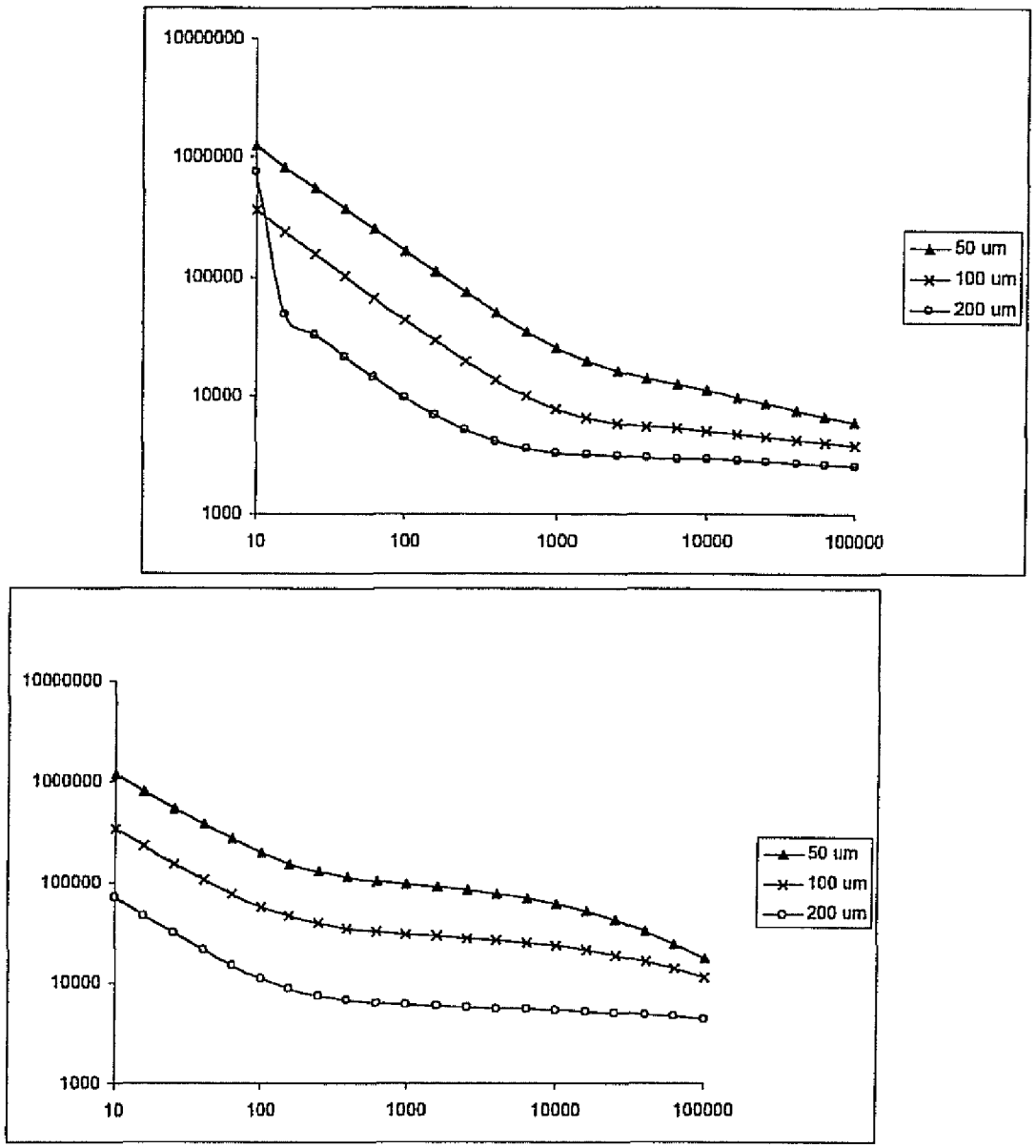
FIG. 4 is a set of graphs showing the relationship of impedance modulus vs. electrode diameter in vitreous and on the retina.

FIG. 3 depict the impedance and phase as a function of frequency for the different sized electrodes when the device was in the vitreous cavity versus tacked to retina. In general, the plots are similar to other microelectrode impedance data. FIG. 3 shows impedance modulus (left column) and phase (right column) for 50 (top), 100 (middle) and 200 (bottom) μm diameter electrodes in the vitreous and on the retina. The impedance modulus is higher when the device is on the retina versus when the device is in the vitreous, but only at higher frequency. In this frequency region, the impedance modulus is not highly dependent on frequency, suggesting more resistive impedance. With decreasing frequency, impedance modulus becomes more frequency dependent, suggesting capacitive impedance in this region. Similarly, the phase is different at higher frequencies but converges to a capacitive phase at lower frequencies. Modeling results suggest that the capacitive phase at the highest frequency, when the device was on the retina for 50 μm and 100 μm electrodes, was due to parasitic capacitance inherent in the measurement. Impedance increased with decreasing electrode size for both vitreous and retina electrodes (FIG. 4). FIG. 4 shows especially impedance modulus versus size in vitreous (left) and on retina.

Figure 5:
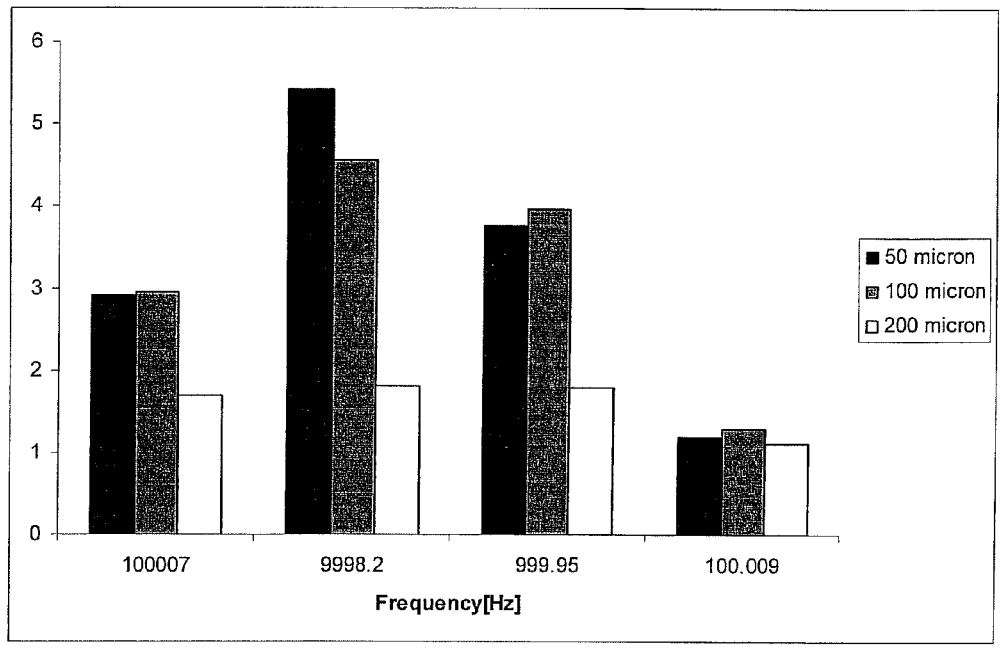
FIG. 5 is a bar graph showing the relationship of impedance modulus vs. frequency at various electrode diameters.

FIG. 5 shows the ratio between impedance modulus when the electrode is against the retina versus impedance modulus when the electrode array is in mid vitreous. The average impedance modulus values for all the electrodes of a particular size were used for the ratios. The ratios indicate that the impedance modulus is between 3 and 6 times higher from the 50 and 100 μm diameter electrodes when the electrode is on the surface of the retina. The 200 μm diameter electrode impedance modulus increased less dramatically but still increased between 1.5 and 2 times. These increases were noted at 100 kHz, 10 kHz, and 1 kHz, but by 100 Hz, the impedance modulus was virtually unchanged between vitreous and retina electrodes. FIG. 5 especially shows—Ratio of Zmod [retina]/Zmod [vitreous] at 4 frequencies.

Since electrical stimulation uses a high frequency signal, the impedance data was limited to 10 Hz-100 kHz. In this range, the electrode-tissue circuit model reduces to two elements in series: the tissue resistance and the CPE. To account for parasitic capacitance in the long lead wire, a parallel capacitor was added across the entire model. The average parameter values for each model element are listed in table I. The average series resistance ($R_u$) was 8.6, 6.7, and 2 times larger on the retina for the 50, 100, and 200 μm electrodes, respectively. The CPE magnitude $Y_o$ was not as position dependent and the CPE exponent n is close to 1, indicating a mostly capacitive CPE. The parasitic capacitance was independent of the test conditions, suggesting a systemic capacitance.

TABLE 1

Circuit model parameters predicted from Impedance and Pulse Data

| Size (Location) | $R_u$ (Kilo Ohms) from EIS | $Y_0$ (nano Siemens) | n | $C_{parasitic}$ (pico Farads) |
|---|---|---|---|---|
| 50 (retina) | 74.35 | 29.975 | 0.824 | 99.0125 |
| 100 (retina) | 30.69 | 99.575 | 0.842 | 105.546 |
| 200 (retina) | 5.415 | 388.623 | 0.887 | 117.2 |
| 50 (vitreous) | 8.623 | 24.245 | 0.856 | 150.075 |
| 100 (vitreous) | 4.596 | 66.511 | 0.907 | 138.91 |
| 200 (vitreous) | 2.749 | 319.15 | 0.905 | 125.59 |

Figure 6:
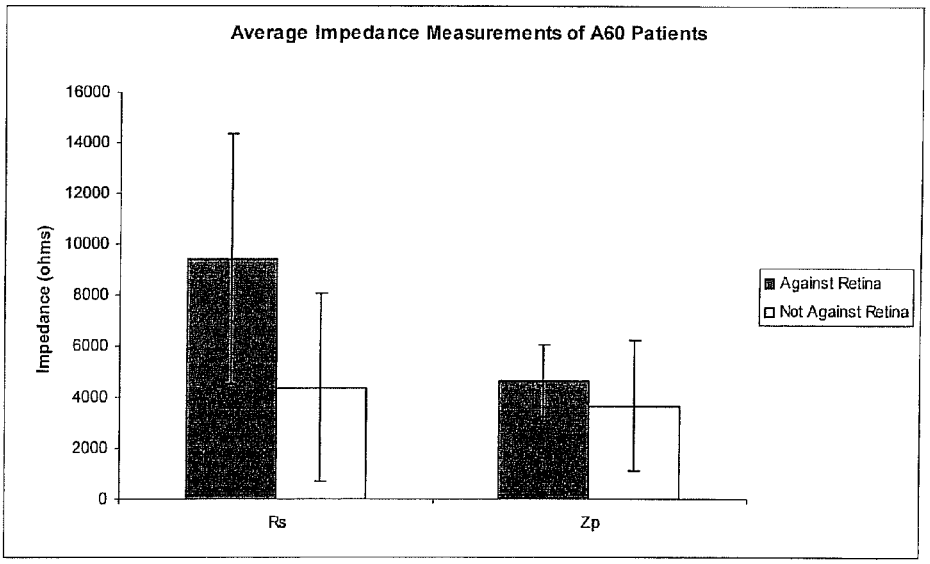
FIG. 6 shows an average impedance measurement of a patient.

FIG. 6 is an impedance component of A60 Patient data—Rs and Zp. The increase of overall impedance due to tissue is mostly due to increase of the Rs component of impedance.

Figure 7:
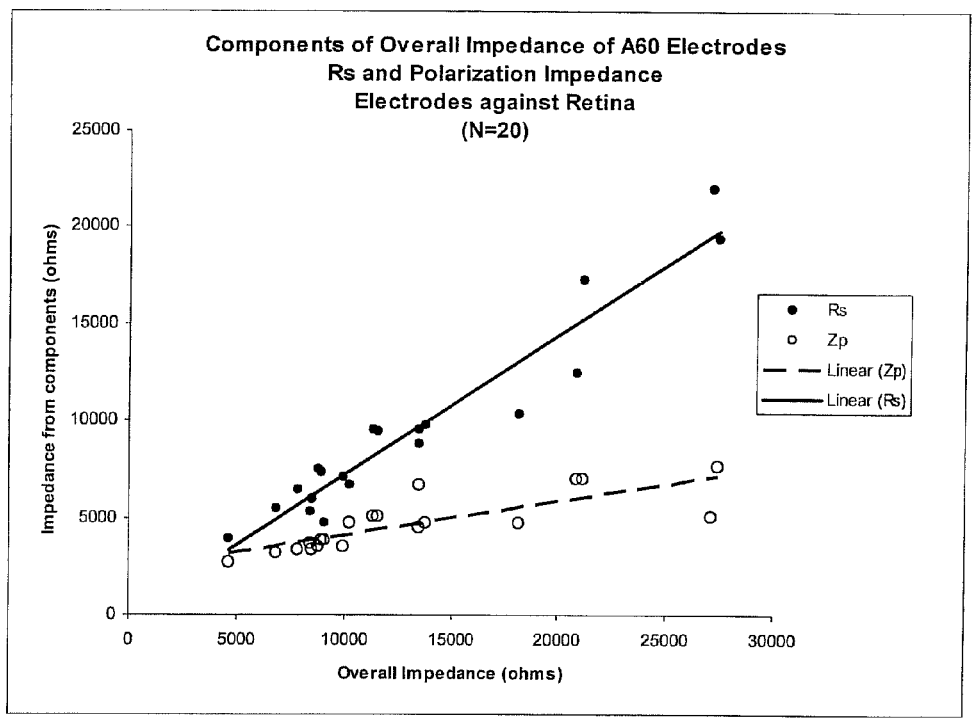
FIG. 7 shows RS and polarization impedance electrodes against the retina.

FIG. 7 is an overall impedance increase of electrodes against retinal tissue shows a great contribution from series resistance component compared to impedance from polarization impedance.

Impedance measurement is a method of monitoring the electrical status of an electrode and its adjacent electrolyte environments. After implantation, some electrodes show an increase in overall impedance. By analyzing the voltage waveform data, one can analyze the overall impedance in terms of its component impedances: series resistance and polarization impedance. Series resistance (Rs) is a measure of the adjacent tissue environment, while the polarization impedance is a measure of the surface quality of the electrode. The current data from six A60 patients suggest that the increase in impedance after implantation is mainly due to an increase in the series resistance component of the overall impedance and less from the polarization impedance.

OCT data from six A60 patients show 20 electrodes that are in direct contact with retinal tissue. The voltage waveform data of these 20 electrodes were analyzed to determine the series resistance (Rs) and polarization impedance (Zp) components of the overall impedance (Zt). Comparison with series resistance and polarization impedance of electrodes not in contact with retina shows that the overall impedance increase of the electrodes against retina have a greater component from the increase in series resistance, see FIG. 6. Similarly, when data is analyzed by individual electrodes in contact with the retina tissue, increase in overall impedance is seen to be directly correlated with increase in Rs, see FIG. 7.

Neural stimulator design must consider the tissue load impedance as part of the design because of Ohm's law V=IR. For a given V set by the chip voltage supply, the tissue impedance R will limit the current output I. While designing a chip with a large voltage supply is one strategy to ensure sufficient I, the cost of that approach is higher power consumption, a larger chip, and possible thermal dissipation issues in the body. Usually it is noted a limit of 20 mW thermal dissipation for a resistive load placed on the retina. There have been modeled chips operating in the eye and have noted similar power limits. It is also possible to limit I, by increasing the pulse duration of the stimulus. There may be perceptual advantages to longer stimulation and lower compliance voltages can also be used. However, longer pulses are inefficient for neural stimulation compared to shorter pulses, so the energy consumption of the device would increase, requiring larger power telemetry components. Thus, a thorough characterization of the load impedance for the neural stimulator is needed to optimize the interface and the overall system.

It was noted that the resistance of the retina was greater than that of the vitreous. This is in agreement with other studies that correlated psychophysical threshold and electrode impedance in humans with prototype retinal implants. Those studies found a trend towards higher impedance for electrodes with lower thresholds. Both higher impedance and lower thresholds suggest that an electrode is closer to the retina. Thus, there are positive and negative consequences of having the electrode near the retina. A higher resistance will increase power consumption but a lower threshold requirement will decrease power consumption. Since it is also desirable to limit the area of retina activated for higher acuity, a closer proximity for the electrode is best and stimulation systems will need to take into account higher impedance. The reasons for higher retinal impedance versus vitreous can be found in the anatomy. In general, neural tissue has higher resistivity than saline. However, the retina has unique structures that may further increase the impedance. The retina, if considered as a material, can be described as a laminated structure with each layer having different electrical conductivity. In particular, the inner limiting membrane and the retina pigment epithelium have been found to have higher resistivity than other parts of the retina.

Circuit models can provide useful information for system design of neural stimulators. With respect to the tissue resistance, the data obtained from small signal impedance data, obtained using a 10 mV sine wave, can be reasonably extrapolated to the large signal response, where the voltage across the tissue can be several Volts. However, the electrode capacitance in general increases with increasing current density, so care must be taken when using circuit models from impedance data as model loads for circuit design. Impedance data will underestimate the available capacitance for stimulation. Therefore, using impedance data to estimate the required voltage for a stimulator chip may result in higher voltage than is actually needed.

Electrode impedance is strongly influenced by the location of the electrode in the eye. An electrode in close apposition to the retina will have significantly higher impedance. This will increase the power requirements for an implanted stimulator. Understanding the electrical interface between a retinal prosthesis and the retina is an important part of optimizing the interface and the implanted system.

Accordingly, what has been shown is an improved method making a hermetic package for implantation in a body. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

We claim:

1. A method of optimizing an electrode tissue interface comprising:
    implanting at least one electrode in the vicinity of visual neural tissue;
    electrically stimulating the visual neural tissue through the at least one electrode, wherein a stimulation signal to each electrode comprises one or more pulses, and wherein frequency of each of the one or more pulses is within a first frequency range;
    measuring impedance of the electrode tissue interface to obtain an impedance measurement;
    adjusting the frequency of at least one pulse in the one or more pulses to be within a second frequency range based on said impedance measurement, wherein the second frequency range is narrower than the first frequency range; and
    altering location of said at least one electrode based on said impedance measurement and said second frequency range.

2. The method of claim 1, wherein distance between neighboring electrodes is from 1 mm-5 mm.

3. The method of claim 2, wherein the distance between neighboring electrodes is from 2 mm-3 mm.

4. The method of claim 3, wherein the distance between neighboring electrodes is from 2.2 mm-2.5 mm.

5. The method of claim 1, wherein the diameter of the at least one electrode is from 10 μm to 250 μm.

6. The method of claim 5, wherein the diameter of the at least one electrode is from 40 μm to 250 μm.

7. The method of claim 1, wherein the electrode spacing is from 600 μm to 1000 μm center to center in the horizontal and vertical direction.

8. The method of claim 1, wherein the altering is from a first location to a second location, and wherein impedance of the electrode tissue interface is higher at the second location than at the first location.

9. The method of claim 1, further comprising adjusting at least one of amplitude and duration of a full set or subset of the one or more pulses based on said impedance measurement.

10. The method of claim 1, further comprising adjusting at least one of arrangement and dimensions of electrodes in the at least one electrode based on said impedance measurement.

11. The method of claim 1, wherein the first frequency range is from 10 Hz to 100 kHz.

12. The method of claim 1, further comprising modeling the electrode tissue interface using a circuit model, the circuit model comprising a series resistance and a polarization impedance, wherein:
    the value of each of the series resistance and the polarization impedance is based on the impedance measurement, and
    the series resistance is a function of the location of the at least one electrode and the polarization impedance is a function of surface quality of each electrode in the at least one electrode.

13. The method of claim 12, wherein the altering is further based on the series resistance.

14. The method of claim 12, further comprising adjusting the surface quality of a full set or subset of electrodes in the at least one electrode to increase the polarization impedance.

15. The method of claim 1, further comprising modeling the electrode tissue interface using a circuit model, wherein:
    the circuit model comprises a series resistance and a constant phase element in series, and the magnitude and phase of each of the series resistance and the constant phase element is a function of the impedance measurement.

16. The method of claim 15, wherein the series resistance ranges from 1 kilo ohm to 80 kilo ohms.

17. The method of claim 15, wherein the magnitude of the constant phase element ranges from 20 nano siemens to 400 nano siemens.

* * * * *